US009757460B2

(12) United States Patent
Günther et al.

(10) Patent No.: US 9,757,460 B2
(45) Date of Patent: Sep. 12, 2017

(54) STABILISED PROTEIN COMPOSITIONS BASED ON SEMIFLUORINATED ALKANES

(71) Applicant: Novaliq GmbH, Heidelberg (DE)

(72) Inventors: Bernhard Günther, Dossenheim (DE); Bastian Theisinger, Mannheim (DE); Sonja Theisinger, Mannheim (DE); Dieter Scherer, Laufen (CH); Clive Wilson, Glasgow (GB); Anthony Pettigrew, Heidelberg (DE); Annette Hüttig, München (DE)

(73) Assignee: NOVALIQ GMBH, Heidelberg (DE)

( * ) Notice: Subject to any disclaimer, the term of this patent is extended or adjusted under 35 U.S.C. 154(b) by 65 days.

(21) Appl. No.: 14/373,877

(22) PCT Filed: Jan. 22, 2013

(86) PCT No.: PCT/EP2013/051163
§ 371 (c)(1),
(2) Date: Jul. 22, 2014

(87) PCT Pub. No.: WO2013/110621
PCT Pub. Date: Aug. 1, 2013

(65) Prior Publication Data
US 2014/0369993 A1 Dec. 18, 2014

(30) Foreign Application Priority Data
Jan. 23, 2012 (EP) .................................... 12152159

(51) Int. Cl.
A61K 47/06 (2006.01)
A61K 38/28 (2006.01)
A61K 47/24 (2006.01)
A61K 38/23 (2006.01)
A61K 38/38 (2006.01)
A61K 38/48 (2006.01)
A61K 9/00 (2006.01)

(52) U.S. Cl.
CPC .............. A61K 47/06 (2013.01); A61K 38/23 (2013.01); A61K 38/28 (2013.01); A61K 38/385 (2013.01); A61K 38/4826 (2013.01); A61K 47/24 (2013.01); A61K 9/0019 (2013.01); A61K 9/0048 (2013.01); C12Y 304/21001 (2013.01)

(58) Field of Classification Search
None
See application file for complete search history.

(56) References Cited

U.S. PATENT DOCUMENTS 2,616,927 A 11/1952 Kauck et al.
5,077,036 A 12/1991 Long
5,326,566 A 7/1994 Parab
5,336,175 A 8/1994 Mames
5,518,731 A 5/1996 Meadows
5,667,809 A 9/1997 Trevino et al.
5,874,469 A 2/1999 Maniar et al.
5,981,607 A 11/1999 Ding et al.
6,042,845 A 3/2000 Sun et al.
6,113,919 A 9/2000 Reiss et al.
6,159,977 A 12/2000 Reeves
6,177,477 B1 1/2001 George et al.
6,197,323 B1 3/2001 Georgieff
6,224,887 B1 5/2001 Samour et al.
6,262,126 B1 7/2001 Meinert
6,372,243 B2 4/2002 Kobuch
6,391,879 B1 5/2002 Reeves
6,458,376 B1 10/2002 Meadows
6,486,212 B2 11/2002 Meinert
6,489,367 B1 12/2002 Meinert
6,730,328 B2 5/2004 Maskiewicz et al.
7,001,607 B1 2/2006 Menz et al.
7,258,869 B1 8/2007 Berry et al.
7,740,875 B2 6/2010 Dechow
8,029,977 B2 10/2011 Meinert et al.
8,470,873 B2 6/2013 Chen
8,614,178 B2 12/2013 Theisinger et al.
8,986,738 B2 3/2015 Meinert
9,308,262 B2 4/2016 Günther et al.
2002/0128527 A1 9/2002 Meinert (Continued)

FOREIGN PATENT DOCUMENTS

EP 0 670 159 A1 9/1995
EP 0 965 329 A1 12/1999

(Continued)

OTHER PUBLICATIONS

Ahmed, I. et al., "Disposition of Timolol and Inulin in the Rabbit Eye Following Corneal Versus Non-Corneal Absorption," International Journal of Pharmaceutics, 1987, 38, 9-21.
Chemical Book, 5-Fluorouracil, available at <http://www.chemicalbook.com/ChemicalProductProperty_EN_CB8162744.htm>, accessed Mar. 7, 2014, 1 page.
Davies, N. "Biopharmaceutical Considerations in Topical Ocular Drug Delivery," Clinical and Experimental Pharmacology and Physiology, 2000, 27, 558-562.
Dembinski, R. et al., "Semi-fluorinated Alkanes as Carriers for Drug Targeting in Acute Respiratory Failure," Experimental Lung Research, 2010, 36, 499-507.

(Continued)

Primary Examiner — David J Blanchard
Assistant Examiner — Daniel F Coughlin
(74) Attorney, Agent, or Firm — Hoxie & Associates LLC

(57) ABSTRACT

The invention provides novel compositions of bioactive polypeptides and proteins with improved stability and shelf-life. The compositions are based on liquid vehicles selected from semifluorinated alkanes. These vehicles are remarkably effective in protecting polypeptides and proteins from degradation and/or aggregation. The compositions are useful for topical administration, e.g. into an eye, or by parenteral injection, e.g. via the subcutaneous or intramuscular route.

16 Claims, 5 Drawing Sheets

(56) References Cited

U.S. PATENT DOCUMENTS

| | | | |
|---|---|---|---|
| 2002/0198266 A1* | 12/2002 | Meinert | A61K 9/0014 514/743 |
| 2003/0018044 A1 | 1/2003 | Peyman | |
| 2003/0027833 A1 | 2/2003 | Cleary et al. | |
| 2004/0266702 A1 | 12/2004 | Dawson et al. | |
| 2005/0079210 A1 | 4/2005 | Gupta | |
| 2005/0175541 A1 | 8/2005 | Lanza et al. | |
| 2008/0207537 A1 | 8/2008 | Turner et al. | |
| 2010/0008996 A1* | 1/2010 | Meinert | 424/489 |
| 2010/0226997 A1 | 9/2010 | Bowman et al. | |
| 2010/0274215 A1 | 10/2010 | Wong et al. | |
| 2012/0010280 A1 | 1/2012 | Aleo et al. | |
| 2012/0095097 A1 | 4/2012 | Tabuchi et al. | |
| 2012/0238639 A1 | 9/2012 | Theisinger et al. | |
| 2013/0266652 A1 | 10/2013 | Theisinger et al. | |
| 2013/0303473 A1 | 11/2013 | Wilson | |
| 2014/0004197 A1 | 1/2014 | Theisinger et al. | |
| 2014/0100180 A1 | 4/2014 | Gunther et al. | |
| 2014/0140942 A1 | 5/2014 | Gunther et al. | |
| 2015/0224064 A1 | 8/2015 | Günther et al. | |
| 2015/0238605 A1 | 8/2015 | Günther et al. | |
| 2016/0101178 A1 | 4/2016 | Wilson | |
| 2016/0159902 A1 | 6/2016 | Günther et al. | |

FOREIGN PATENT DOCUMENTS

| | | | |
|---|---|---|---|
| EP | 0 965 334 A1 | 12/1999 | |
| EP | 0 939 655 B1 | 6/2002 | |
| EP | 1 152 749 B1 | 4/2006 | |
| EP | 2 110 126 A1 | 10/2009 | |
| EP | 2 332 525 A1 | 6/2011 | |
| EP | 2 335 735 A1 | 6/2011 | |
| EP | 2462921 A1 | 6/2012 | |
| GB | WO 2010146536 A1 * | 12/2010 | A61K 9/10 |
| JP | S6452722 | 2/1989 | |
| JP | 2000511157 | 8/2000 | |
| WO | WO 96/40052 A1 | 12/1996 | |
| WO | WO 97/12852 A1 | 4/1997 | |
| WO | WO 00/24376 A1 | 5/2000 | |
| WO | WO 00/54588 A1 | 9/2000 | |
| WO | WO 02/49631 A1 | 6/2002 | |
| WO | WO 2005/099718 A1 | 10/2005 | |
| WO | WO 2005/099752 | 10/2005 | |
| WO | WO 2005/123035 A1 | 12/2005 | |
| WO | WO 2006/007510 A1 | 1/2006 | |
| WO | WO 2006/042059 | 4/2006 | |
| WO | WO 2007/052288 A2 | 5/2007 | |
| WO | WO 2008/060359 A2 | 5/2008 | |
| WO | WO 2010/062394 A2 | 6/2010 | |
| WO | WO 2011/073134 A1 | 6/2011 | |
| WO | WO 2012/052418 A1 | 4/2012 | |
| WO | WO 2012/062834 A1 | 5/2012 | |
| WO | WO 2012/093113 A1 | 7/2012 | |
| WO | WO 2012/121754 | 9/2012 | |
| WO | WO 2012/160179 A2 | 11/2012 | |
| WO | WO 2012/160180 A2 | 11/2012 | |
| WO | WO 2014/041055 A1 | 3/2014 | |
| WO | WO 2014/041071 A1 | 3/2014 | |
| WO | WO 2015/011199 | 1/2015 | |

OTHER PUBLICATIONS

Elkeeb, R. et al., "Transungual Drug Delivery: Current Status," International Journal of Pharmaceutics, 2010, 384, 1-8.
Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.
Gayton, J., "Etiology, Prevalence, and Treatment of Dry Eye Disease," Clinical Ophthalmology, 2009, 3, 405-412.
Griffin, W., "Classification of Surface-Active Agents by 'HLB'," Journal of the Society of Cosmetic Chemists, 1949, 1, 311-326.
Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).
Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.
International Preliminary Report on Patentability for International Application No. PCT/EP2011/068141 dated Apr. 23, 2013, 4 pages.
International Preliminary Report on Patentability for International Application No. PCT/EP2011/069795 dated May 14, 2013, 8 pages.
International Preliminary Report on Patentability for International Application No. PCT/EP2012/050043 dated Jul. 10, 2013, 5 pages.
International Preliminary Report on Patentability for International Application No. PCT/EP2012/059787 dated Nov. 26, 2013, 9 pages.
International Preliminary Report on Patentability for International Application No. PCT/EP2012/059788 dated Nov. 26, 2013, 8 pages.
International Preliminary Report on Patentability for International Application No. PCT/EP2013/051163 dated Jul. 29, 2014, 7 pages.
International Search Report for International Application No. PCT/EP2011/068141 mailed Dec. 14, 2011, 2 pages.
International Search Report for International Application No. PCT/EP2011/069795 mailed Jan. 16, 2012, 3 pages.
International Search Report for International Application No. PCT/EP2012/050043 mailed Apr. 24, 2012, 2 pages.
International Search Report for International Application No. PCT/EP2012/059787 mailed Dec. 5, 2012, 4 pages.
International Search Report for International Application No. PCT/EP2012/059788 mailed Dec. 3, 2012, 4 pages.
International Search Report for International Application No. PCT/EP2013/051163 mailed Mar. 4, 2013, 4 pages.
Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.
Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.
Lemp, M., "Management of Dry Eye Disease," The American Journal of Managed Care, 2008, 14 (3), S88-S101.
Mackiewicz, J. et al., "In Vivo Retinal Tolerance of Various Heavy Silicone Oils," Investigative Ophthalmology & Visual Science, 2007, 48 (4), 1873-1883.
Meinert, H. et al., "The Use of Semifluorinated Alkanes in Blood-Substitutes," Biomaterials, Artificial Cells, and Immobilization Biotechnology, 1993, 21 (5), 583-595.
Meinert, H. et al., "Semifluorinated Alkanes—A New Class of Compounds with Outstanding Properties for Use in Ophthalmology," European Journal of Ophthalmology, 2000, 10 (3), 189-197.
Murdan, S., "Enhancing the Nail Permeability of Topically Applied Drugs," Expert Opinion on Drug Delivery, 2008, 5 (11), 1267-1282.
Perry, H., "Dry Eye Disease: Pathophysiology, Classification, and Diagnosis," The American Journal of Managed Care, 2008, 14 (3), S79-S87.
Pinarci, E. et al., "Intraocular Gas Application in the Diagnosis and Treatment of Valsalva Retiopathy in Case with Premacular Hemorrhage," XP002625604, Retina-Vitreus, 2009, 17 (2), 153-155, abstract only.
Rosca-Casian, O. et al., "Antifungal Activity of *Aloe vera* Leaves," Fitoterapia, 2007, 28, 219-222.
Rosenberg, A., "Effects of Protein Aggregates: An Immunologic Perspective," The AAPS Journal, 2006, 8 (3), E501-E507.
Stevenson, C., "Characterization of Protein and Peptide Stability and Solubility in Non-Aqueous Solvents," Current Pharmaceutical Biotechnology, 2000, 1, 165-182.
Wang, W., "Lyophilization and Development of Solid Protein Pharmaceuticals," International Journal of Pharmaceutics, 2000, 203, 1-60.
Wong, D. et al., "Perfluorocarbons and Semifluorinated Alkanes," Seminars in Ophthalmology, 2000, 15 (1), 25-35.
Gerdenitsch, "Emulsions—established and promising drug carriers for parenteral adminstration", retrieved from internet: http:/

(56) References Cited

OTHER PUBLICATIONS ipimediaworld.com/wp-content/uploads/2012/05/Pages-from-IPI-Volume-2-Issue-1-11.pdf. Date Accessed: Jul. 20, 2016.
JP 2000511157A, English Machine Translation of the Abstract, Description, and Claims, Espacenet, Date Accessed: Feb. 10, 2016.
JPS6452722, English Machine Translation of the Abstract, Description, and Claims, Espacenet, Date Accessed: Feb. 10, 2016.
U.S. Appl. No. 14/427,927, filed Mar. 12, 2015, Gunther.
U.S. Appl. No. 14/427,969, filed Mar. 12, 2015, Gunther.
Baerdemaeker, L. et al., "Pharmacokinetics in Obese Patients," Continuing Education in Anaesthesia, Critical Care & Pain, 2004, 4, 152-155.
Broniatowski, M. et al., "Langmuir Monolayers Characteristic of (Perfluorodecyl)-Alkanes," Journal of Physical Chemistry B, 2004, 108, 13403-13411.
English-language machine translation of EP0670159 (A1) issued in U.S. Appl. No. 14/122,025 on Apr. 1, 2015, 10 pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.
International Search Report for International Application No. PCT/EP2013/068882 mailed Oct. 30, 2013, 4 pages.
International Search Report for International Application No. PCT/EP2013/068909 mailed Dec. 5, 2013, 4 pages.
Plassmann, M. et al., "Trace Analytical Methods for Semifluorinated n-Alkanes in Snow, Soil, and Air," Analytical Chemistry, 2010, 82 (11), 4551-4557.
Plassmann, M. et al., "Theoretical and Experimental Simulation of the Fate of Semifluorinated n-Alkanes During Snowmelt," Environmental Science & Technology, 2010, 44 (17), 6692-6697.

\* cited by examiner

STABILISED PROTEIN COMPOSITIONS BASED ON SEMIFLUORINATED ALKANES

FIELD

The present invention is in the field of peptide and protein compositions, in particular compositions which are useful as pharmaceutical formulations of polypeptides or proteins for therapeutic or diagnostic use.

BACKGROUND

New classes of therapeutic biopharmaceuticals based on peptides and proteins targeting previously non-treatable or incurable diseases have emerged in recent years, in consequence of the many new advances and developments that have arisen in the biotechnological field.

However, due to their poor oral bioavailability and general short half-lives in vivo, the delivery method of many of the proteins and polypeptide therapeutics developed thus far has been mostly restricted to the parenteral route. The human monoclonal antibodies (a rapidly growing class of targeted therapeutics) that are currently approved all require administration by injection. For example, adalimumab (Humira™, marketed by Abbott), a human monoclonal antibody first indicated for treating rheumatoid arthritis, is presented in a pre-filled syringe. Only a few oral, mucosal or inhalative therapeutic compositions are currently commercially available, many of which incorporate only relatively lower molecular weight polypeptide agents. An example of a higher molecular weight protein therapeutic delivered by inhalation route is dornase alfa (Pulmozyme™, distributed by Roche), a solution of recombinant human deoxyribonuclease I, indicated for the treatment of cystic fibrosis.

The sheer molecular size and complexity of proteins and polypeptides as well as the relative ease in loss of their activity through damage to their structural integrity poses a challenge for the processing, formulation, and delivery of these types of therapeutics.

The biological activity of a protein is dictated by its one-of-a-kind three-dimensional structure; by its secondary and tertiary structures. A specific and balanced combination of internal interactions such as hydrogen-bonding, electrostatic interactions, van der Waals forces, hydrophobic interactions, and covalent bonding between the peptide chain components encompassing the protein is what contributes to the final structure of a folded protein in its native state. Marginal changes to these interactions can potentially have a big impact on the structural integrity of a protein. The precise biological function of a protein is based on its specific interactions with other relevant macromolecules and/or small molecules. Consequently, the specificity and thus the therapeutic effectiveness of a protein will be lost, if essential three-dimensional characteristics are disrupted in any way.

The loss of native protein structure can occur through a number of degradative pathways. Aggregation can occur through non-covalent bonding events such as the self-association of native protein monomers, or the association of partially unfolded proteins into non-native oligomers. Protein deterioration and aggregation can also occur through covalent, irreversible chemical events such as the formation of and/or exchange of cross-linking disulphide bonds, peptide-bond hydrolysis, deamidation, or oxidation. The prevalence of these phenomena not only depends on the inherent characteristics of the protein, but also on a number physicochemical environmental conditions such as temperature including related stress conditions like freeze-thaw cycles, pH, protein concentration, ionic strength, the presence of destabilizing chemical additives, dryness and mechanical stress factors such as cavitation or shear, all of which can negatively impact the native folded structure of the protein.

The association of protein into such oligomeric, often high molecular weight forms poses a major problem in the formulation, delivery and long-term storage of protein or polypeptide therapeutics. Aggregation can lead to the loss of active protein drug, leading to unreliable and ineffective dosages. In liquid formulations, aggregates which may be insoluble can precipitate and form large particulates can impede flow, which would be extremely disadvantageous for parenteral applications. Furthermore, protein aggregates may exhibit toxicity and can trigger undesirable immunogenic responses (Rosenberg, A. S., AAPS J, 2006, 8, E501). The characteristics of the medium chosen for a protein or polypeptide liquid formulation can thus have a major impact towards the practicality and longevity of a formulation.

An aqueous environment is known to be important in most cases for the maintenance of protein structure and bioactivity, i.e. water molecules can be essential or even the driving force for folding and/or may play a direct role in enzymatic activity. On the other hand, an aqueous medium may also have an adverse effect, depending on the nature of the composition of the aqueous phase and various parameters such as pH and ionic strength. Water can act as a plasticizer or serve as the reaction medium as well as directly as a reaction component, such as in the hydrolytic cleavage of amide bonds. Thus, a method which has been substantially used in the field of formulating protein therapeutics is lyophilisation (freeze-drying) or spray-drying the protein to a solid-state powder form. In this case, the removal of water restricts the conformational flexibility and diffusive mobility of the protein macromolecule to interact with others, thus diminishing the chances of aggregation. Consequently, with proteins in the dry state, substantially longer-term storage is feasible, in comparison to many aqueous-based formulations.

However, it should be noted that protein degradation and aggregation can occur quite easily during the process of lyophilisation itself, and so to decrease the incidence of these events, time input and costs for developing the lyophilisation process are necessarily quite high. Additional stabilizers such as saccharides, polyols and the like, which serve to compensate the loss of water hydrogen-bonding effects are also often added into the pre-lyophilisation composition. Such excipients, while useful during the lyophilisation process may be detrimental to protein stability in the dry state over time, for instance by phase separation via crystallization. Other post-lyophilisation stabilizing excipients may also need to be included in order to support the longer shelf-life of the protein, adding to the number of components that have to be present in the final formulation.

Also, despite the removal of water, dry state protein compositions are not immune to the effects of external environmental factors such as temperature, and chemical degradation reactions where water is not a key reagent, such as deamidation or oxidation. Elevated temperatures result in increased mobility and consequently a greater likelihood for inter-protein reactions, thus many lyophilized proteins still have to be stored at all times under refrigerated conditions. Also, excipients added to render the pH and tonicity of the formulation more amenable for the lyophilisation process may not be as stabilizing for the protein in the final dry state. The introduction of moisture may be a concern, and particular attention must also be given to the storage means (as well as material) for proteins in the dry solid state.

Furthermore, the reconstitution of the lyophilized protein in aqueous media as an extra step prior to actual administration is necessary, and carries the risk of improper handling/dosing and contamination. The reconstitution step itself may trigger protein aggregation, if the pH, or temperature of the aqueous medium is not optimal or the time for proper rehydration is too short. Thus, the formulation of a suitable reconstitution medium may also need to be considered and properly developed. Overall, from an economical viewpoint, a significantly large amount of time, effort and cost are involved for the process and formulation development of lyophilized protein compared to liquid formulations (Wang, W., Int. J. Pharm., 2000, 203, 1).

The use of organic solvents as carrier media is another option for formulating protein therapeutics. It should be noted, however that such solvents may not always have a stabilizing effect on protein structure, in some cases, rather the opposite. For example, at higher concentrations, strongly polar solvents such as DMSO or DMF and alcohols such as methanol or ethanol can act as denaturants, often by competing with internal amide hydrogen-bonding which may lead to the loss of tertiary structures; even the ratio of secondary structures may be altered, possibly leading to non-native structures (Stevenson, C. L., Curr. Pharm. Biotech., 2000, 1, 165). Consequently, such solvents may not be ideal for the long-term storage of protein therapeutics. Similarly, the physiological tolerability of these types of solvents may be low, and further considerations as to the release and adsorption of the protein (also depending on the state of its solubility in such solvent systems) need to be taken into consideration.

Protein therapeutic formulations in aqueous media are often simply available in the form of a solution. Formulations using organic solvents, on the other hand, require further consideration due to the general non- or partial-solubility of the protein in such media, depending on solvent polarity and physical properties of the protein. The combination of hydrophobic organic solvents and water-free (lyophilized) protein usually produces dispersions or suspensions. In such cases, the long-term physical stability of the suspension is also an important consideration during formulation development, alongside with the long-term stability of the protein itself. The use of non-polar solvents such as oils and lipids as suspension carriers for proteins or polypeptides for parenteral use has been reported, however the stability of these carriers at physiological temperatures over extended periods of time has been questioned (Knepp, V. M. et al, Pharm. Res. 1998, 15, 1090). Further, these compounds may cause side effects as pain at injection site. Also, oils and lipids tend to strongly retard the release of therapeutic agent. This may be a useful characteristic for effecting longer term sustained release or depot-type injectable formulations, but not if a more rapid and immediate bioavailability is desired.

Polymer-based compositions have also been described, for example, viscous non-aqueous suspension formulations of protein or peptide agents, suitable for use in conjunction with an implantable device, comprising polyvinylpyrrolidone as a polymer component and lauryl lactate (or lauryl alcohol) as a solvent have been reported (U.S. Pat. No. 7,258,869 and EP1152749). Such compositions are suggested to be suited for the sustained release of such therapeutic agents.

Perfluorinated compounds have also been used as non-aqueous liquid carriers of protein, polypeptides and other biologically active agents. For example, U.S. Pat. No. 6,458, 376 describes compositions proposed for ophthalmic applications (such as topically applied eye drops) in which therapeutic/diagnostic compounds, including oligopeptides and protein growth factors are suspended in perfluorocarbons and in the presence of at least one surfactant. It is however, silent on the subject of the choice of particular surfactants that can be suitable for use in compositions containing protein or peptide therapeutic compounds, and makes no discussion as to the long-term chemical and physical stability of such particular compounds in these formulations over time.

EP0939655 (and U.S. Pat. No. 6,730,328) discloses thermally stable formulations in which non-aqueous, hydrophobic, non-reactive vehicles such as mineral oil, perfluorodecalin, methoxyfluorane, perfluorotributylamine or tetradecane are used for suspension compositions comprising proteins, proteinaceous compounds and nucleic acids. The formulations are proposed for parenteral, transdermal, mucosal, oral and enteral methods of administration, as well as their use for long-term continuous administration and delivery via an implantable device. However, the ability of these suspension compositions to remain physically stable, i.e. uniformly dispersed or re-dispersible after a length of time was not disclosed. The actual tissue compatibility of these types of compositions has not been demonstrated either.

US 2010/0008996 mentions the inhalative or instillative use of SFAs as carriers for transporting an active substance to the alveolar membrane/lung regions of a patient. More in detail, the document teaches micellar colloidal solutions of active substances which exhibit sufficient solubility in SFAs and whose molecules have a size in the range of 1 to 0.1 nm in order for facilitate transport through the lung membrane to the bloodstream. It discloses SFA-based compositions of the small molecular drugs, ibuprofen, alpha-tocopherol, retinol palmitate, 5-fluorouracil, bromohexine, oseltamivir, and ambroxol, which are described as being useful for inhalation or instillation. In contrast, it does not disclose any specific composition of an active substance which is a larger molecule, such as a protein, or of an active substance which is not soluble in SFAs.

WO 2011/073134 similarly discloses solutions comprising ciclosporin, a cyclic polypeptide with molecular weight of 1202.61 in a semifluorinated alkane, optionally in the presence of a cosolvent such as ethanol. Whilst suspensions and emulsions are also mentioned as optional alternatives, there is no specific disclosure of such type of composition.

Kociok et al. (Graefe's Arch Clin Exp Ophthalmol 2005, 243, 345-358) investigated whether macrophage activation through cell membrane attachment might be supported by emulsified tamponade droplets of a certain vesicle size. For this purposes, they prepared emulsified droplets (referred to as unilamellar vesicles) of F6H8 in an aqueous continuous phase by the extrusion of the semifluorinated alkane through polycarbonate filter membranes into a PBS solution. In order to determine whether human serum albumin (HSA) has an influence on blood neutrophil activation, some of the droplets were coated with HSA by including HSA into the aqueous PBS solution.

It is an object of the present invention to introduce novel protein or polypeptide compositions which overcome the limitations and disadvantages associated with currently known formulations.

SUMMARY OF THE INVENTION

In a first aspect, the invention provides novel compositions of bioactive polypeptides or proteins in a liquid vehicle which comprises a semifluorinated alkane of the formula RFRH, wherein RF is a linear perfluorinated hydrocarbon segment with 4 to 12 carbon atoms, and wherein RH is a linear alkyl group with 4 to 8 carbon atoms.

The bioactive polypeptide or protein preferably has a molecular weight of at least about 1,500 Da, in particular at least about 2,000 Da, and is incorporated into the composition such as to form a dispersion or suspension. The polypeptide or protein is preferably a therapeutic or diagnostic agent or vaccine.

The bioactive compound is preferably a polypeptide or protein which is sensitive to degradation and/or aggregation. It has been found by the inventors that the use of semifluorinated alkane affords more stable dispersions or suspensions of proteins such as insulin compared to other organic solvents. In conjunction, it has also been established that semifluorinated alkanes have a remarkable stabilising effect on such compounds, and that sensitive proteins such as insulin may even be subjected to substantially elevated temperatures without loss of bioactivity through aggregation and/or degradation.

Particularly useful semifluorinated alkanes are selected from the group consisting of F4H5, F4H6, F4H8, F6H4, F6H6, F6H8, and F6H10 according to the terminology as defined herein-below. These semifluorinated alkanes are well tolerated by tissues, capable of dissolving a large range of further excipients that may be required in pharmaceutical compositions, and form—probably due to their inherent amphiphilicity—pharmaceutically advantageous dispersions or suspension with polypeptides and proteins.

In one aspect, the protein or polypeptide compositions of the present invention are chemically and physically stable at room temperature and even at elevated temperatures (e.g. around 37° C., or physiological temperature), whereby bioactivity of the protein or peptide agent is retained and there is insignificant aggregation of the therapeutic agent. In a further aspect, the protein or polypeptide suspension compositions in the present invention also remain monodisperse and/or can be readily re-dispersed after storage at elevated temperatures (e.g. around 37° C., or physiological temperature).

Moreover, the invention provides medical uses of such compositions as well as methods for stabilising polypeptides or proteins which are sensitive to degradation and/or aggregation, which methods include the incorporation of the polypeptide or protein in a liquid vehicle comprising a semifluorinated alkane as defined above.

DETAILED DESCRIPTION OF THE INVENTION

Figure 1:
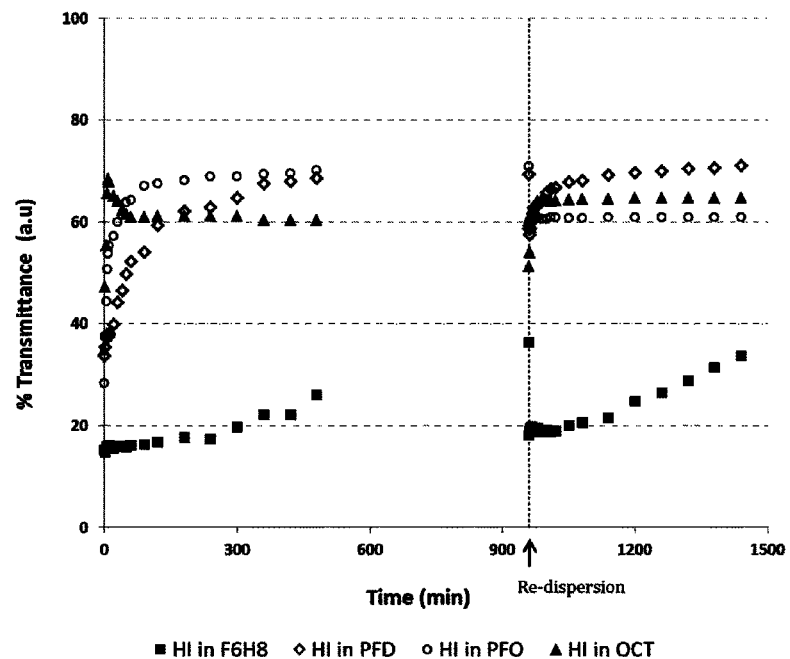
FIG. 1: Retention of turbidity of suspensions of human insulin (HI) in F6H8, perfluorodecalin (PFD), perfluorooctane (PFO), and octane (OCT).

In a first aspect, the invention provides a composition comprising a bioactive compound and a liquid vehicle. The bioactive compound is selected from therapeutic or diagnostic agents or vaccines which are polypeptides and proteins. Preferably, the polypeptide or protein has a molecular weight of at least about 1,500 Da, in particular at least about 2,000 Da. The liquid vehicle comprises a semifluorinated alkane of the formula RFRH, wherein RF is a linear perfluorinated hydrocarbon segment with 4 to 12 carbon atoms, and wherein RH is a linear alkyl group with 4 to 8 carbon atoms. Moreover, the bioactive compound is incorporated in the composition such as to form a dispersion or suspension; i.e., the bioactive compound is dispersed or suspended in the liquid vehicle.

Semifluorinated alkanes are very advantageous vehicles from the pharmaceutical perspective: Firstly, they are substantially non-toxic, i.e. well-tolerated by various types of human and animal tissue after topical administration or injection. Secondly, they are chemically inert and show little detrimental interaction with active or inactive ingredients of pharmaceutical formulations. Thirdly, they are—probably due to their inherent degree of amphiphilicity—capable of dissolving a large range of compounds, such as small molecular active ingredients or many common excipients which are useful in pharmaceutical formulations. Fourthly, when incorporating compounds that are not soluble or only very poorly soluble in semifluorinated alkanes (such as many polypeptides and proteins), they form dispersions or suspensions with very useful physical or pharmaceutical properties, i.e. with little or no tendency to form solid, non-dispersible sediments.

The inventors have found that protein dispersions and suspensions in semifluorinated alkanes are surprisingly stable. They remain finely dispersed and homogeneous, and if flotation or sedimentation takes place, it generally occurs slowly, leaving sufficient time for the patient or care giver to withdraw a dose after shaking the container (e.g. vial) which holds the formulation. The formation of large poorly re-dispersible aggregates is not observed, and after flotation or sedimentation, the protein particles are easily re-dispersed by gentle shaking without significant loss, and appear to largely retain their original particle size distribution.

This is in sharp contrast to other chemically inert liquid vehicles, such as perfluorocarbons, which have been proposed as vehicles for medicines in e. g. U.S. Pat. No. 5,518,731 and U.S. Pat. No. 6,458,376. It has been found by the inventors that when perfluorinated compound such as perfluorooctane or perfluorodecalin or other organic solvents like octane are used as liquid vehicles, the suspensions tend to be significantly more unstable, i.e. they separate very rapidly by flotation of the dispersed phase, or by its sedimentation, depending on the relative densities of the dispersed phase and of the continuous phase. This is accompanied by a rapid formation of particle aggregates which may be dense and are poorly redispersible. Rapid flotation or sedimentation makes precise and reproducible dosing very challenging, if not impossible. For example, if an injectable or ophthalmic suspension settles very rapidly after shaking, the first dosing from a full container (e.g. a vial), if not withdrawn immediately upon shaking, will contain a lower-than-intended number of drug particles, unless the container is held upside down, in which case more than the intended quantity of drug particles will be dispensed. When the same container is nearly empty and the last doses are dispensed, the drug dose withdrawn per volume will be too high if it was low in the beginning, and vice versa.

Moreover, the formation of large and poorly re-dispersible aggregates of proteins in perfluorinated carriers or other organic solvents like octane potentially leads to the clogging of fine injections needles such as those used for subcutaneous injection. Large particles are at risk to induce adverse reactions in the body, in particular inflammation processes.

It was also observed that the particles suspended in perfluorinated compounds or octane tend to adhere to the walls of the glass vial container and/or needle-syringe used for withdrawal of a dose. This too would lead to interference with precise dosing.

The advantageous properties of SFA-based suspensions result in superior pharmaceutical quality and performance characteristics. The level of convenience to the patient and/or health care provider is greatly increased. More importantly, the dosing accuracy, i.e. precision and reproducibility of dosing, is greatly improved over other types of pharmaceutical suspensions. This will bring about a more reliable therapeutic effect and a reduced risk of adverse effects which result from overdosing.

At the same time, the semifluorinated alkanes have a remarkable stabilising effect on polypeptides and proteins. They substantially prevent or inhibit protein aggregation and significantly reduce chemical degradation. In fact, it was found that some sensitive proteins are stabilised to such degree that, when incorporated within a semifluorinated alkane, they can be exposed to high temperatures such as 50° C. without loss of bioactivity. Key advantages of the present invention are brought about by the presence of a semifluorinated alkane in the composition, functioning as a liquid vehicle. Semifluorinated alkanes are linear or branched alkanes some of whose hydrogen atoms have been replaced by fluorine. In the semifluorinated alkanes (SFA's) used in the present invention, one linear non-fluorinated hydrocarbon segment and one linear perfluorinated hydrocarbon segment are present. These compounds thus follow the general formula F(CF2)n(CH2)mH. According to the present invention, n is selected from the range of 4 to 12, and m is selected from the range of 4 to 8.

A nomenclature which is frequently used for SFA's designates a perfluorated hydrocarbon segment as RF and a non-fluorinated segment as RH. Alternatively, the compounds may be referred to as FnHm and FnHm, respectively, wherein F means a perfluorated hydrocarbon segment, H means a non-fluorinated segment. Again and m define the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

SFA's which are useful in the context of the present invention are also described in EP-A 965 334, EP-A 965329 and EP-A 2110126, the disclosure of which documents is incorporated herein.

Preferred SFA's include in particular the compounds F4H5, F4H6, F4H8, F6H4, F6H6, F6H8, and F6H10. Particularly preferred for carrying out the invention are F4H5, F4H6, F6H6 and F6H8. In another particularly preferred embodiment, the composition of the invention comprises F6H8.

Optionally, the composition may comprise more than one SFA. It may be useful to combine SFA's, for example, in order to achieve a particular target property such as a certain density or viscosity. If a mixture of SFA's is used, it is furthermore preferred that the mixture comprises at least one of F4H5, F4H6, F6H4, F6H6, F6H8, and F6H10, and in particular one of F4H5, F4H6, F6H6 and F6H8. In another embodiment, the mixture comprises at least two members selected from F4H5, F4H6, F6H4, F6H6, F6H8, and F6H10, and in particular at least two members selected from F4H5, F6H6 and F6H8.

Liquid SFA's are chemically and physiologically inert, colourless and stable. Their typical densities range from 1.1 to 1.7 g/cm$^3$, and their surface tension may be as low as 19 mN/m. SFA's of the RFRH type are insoluble in water but also somewhat amphiphilic, with increasing lipophilicity correlating with an increasing size of the non-fluorinated segment.

Liquid SFA's of the RFRH type are being used commercially for unfolding and reapplying a retina, for long-term tamponade as vitreous humour substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds. On the other hand, SFA's have not been used as excipients in approved drug products as of today.

The composition of the invention comprises a bioactive compound selected from the group of polypeptides or proteins. Polypeptides and proteins represent polymers of amino acid units that linked to each other by peptide bonds. Since the size boundaries that are often used to differentiate between polypeptides and proteins are somewhat arbitrary, the two expressions for these molecules should—within the context of the present invention—not be understood as mutually exclusive: A polypeptide may also be referred to as a protein, and vice versa. Typically, the term "polypeptide" only refers to a single polymer chain, whereas the expression "protein" may also refer to two or more polypeptide chains that are linked to each other by non-covalent bonds. Preferably, the bioactive compound according to the invention should have a molecular weight of at least about 1,500 Da, in particular at least about 2,000 Da.

As described in more detail above, the bioactivity of polypeptides and proteins not only relies on their primary chemical structure, i.e. their amino acid sequence, but also on their secondary and tertiary structure, often also on their quaternary structure. Often, the sensitivity of a polypeptide or protein to degradation also relates to its secondary, tertiary or even quaternary structure. Polypeptides and proteins that will benefit from the present inventions include both chemically unstable compounds, e.g. compounds that are prone to hydrolysis, as well as compounds that have a tendency to rapidly lose their secondary or higher structure, and/or denature. In particular, the composition comprises a polypeptide or protein that is sensitive to degradation and/or aggregation.

Such sensitivity typically means that the respective compound cannot be formulated as a liquid formulation (e.g. ready for use by injection) in common aqueous media, even when incorporating stabilising excipients (such as buffers etc.), and stored under normal conditions. Thus, pharmaceutical formulations of sensitive compounds, in order to have an acceptable shelf life (of typically at least 2 years) must either be refrigerated during storage, or they must be provided in a dry form from which they are reconstituted prior to use. In particular, "sensitive" means that the respective compound loses at least about 5% of its bioactivity within less than 1 year of storage under normal conditions when formulated in an optimised aqueous vehicle.

In a preferred embodiment, the polypeptide or protein is a therapeutic or diagnostic compound or a vaccine. As used herein, a therapeutic compound is a compound that is useful for preventing a disease or condition, alleviating any symptoms of a disease or condition, improving any disease or condition, delaying the progress of a disease or condition or the like. A diagnostic compound is useful for determining the state of an organism, or for diagnosing a disease, condition, symptom, or patient phenotype. The therapeutic compound must be administered to the patient, whereas the diagnostic agent may be used in vivo or in vitro, depending on the specific case. For the avoidance of doubt, the therapeutic or diagnostic compound is incorporated within the composition of the invention in a therapeutically or diagnostically effective amount.

The inventors have also found that the stabilising effect of the semifluorinated alkanes on the chemical or biological activity is very pronounced if the bioactive compound is a polypeptide or protein in the low- to mid-range of molecular size for therapeutic and diagnostic agents of this class. In one specific embodiment, the molecular weight of the bioactive agent is in the range from about 2,000 to about 100,000 Da. In a further embodiment, the molecular weight is in the range from about 1,000 to about 60,000 Da. In further embodiments; it is in the range from about 2,000 to about 60,000 Da, or from about 5,000 to about 50,000 Da, respectively. On the other hand, the benefit of physical stability and/or easy redispersibility of the dispersion or suspension is also readily achieved with polypeptides and proteins of relatively large molecular size, such as serum albumin (approx. 67 kDa), or even with proteins of more than 100,000 Da. In a further specific embodiment, the bioactive agent is a single-domain protein or a two-domain protein. This is based on the inventors' discovery that the stabilising effect of the semifluorinated alkanes is also very pronounced in combination with such proteins having only one or two domains. As used herein, a protein domain is a part of the protein's amino acid sequence which forms a compact, three-dimensional structure that can evolve, function, and exist somewhat independently of the rest of the protein chain. Domains may substantially vary in length; in most cases, however, they comprise from about 25 to about 500 amino acid monomers.

Optionally, the bioactive agent may be an enzyme, hormone, or growth factor or a structural protein. The composition may comprise a therapeutic hormone which serves to replace or supplement a natural hormone deficient in a patient. The composition may further optionally comprise more than one bioactive polypeptide or protein.

In a further optional embodiment, the bioactive agent may be a protein that is recombinant or a protein which may be from naturally derived source or a synthesised peptide. The protein may also be a protein conjugate or an analogue of a natural and/or endogenous protein.

According to a further embodiment, the composition comprises an insulin as bioactive agent, in particular a recombinant human insulin. It was surprisingly found that insulin dispersed in a semifluorinated alkane is extremely stable and does not aggregate even when stored at substantially elevated temperatures, such as at about 50° C.

As mentioned, the polypeptide or protein is incorporated in the composition such as to form a dispersion or suspension In other words, the polypeptide or protein is dispersed or suspended in the liquid carrier. Whether a suspension is formed upon dispersing the protein in the liquid carrier depends e.g. on the nature of the protein, its concentration in the carrier, and the selected SFA(s).

As used herein, a suspension may be defined as a type of a dispersion, i.e. a system having at least one continuous (or coherent) phase and at least one discontinuous (or inner) phase which is dispersed in the continuous phase. In a suspension, the dispersed phase is in the solid state. The suspensions useful for practising the invention are liquids, at least at physiological temperature, which means that the continuous phase is a liquid. Typically, the suspensions are also liquid at room temperature. Beyond suspensions, the term dispersions is understood to include colloidal systems in which a protein and polypeptide is finely dispersed in the liquid phase. In some embodiments, the polypeptide or protein is also at least partially solvated.

In one particular embodiment, the composition comprises only the bioactive polypeptide or protein and one or more SFAs, i.e. the composition consists of the bioactive polypeptide or protein and one or more SFAs as defined above.

In contrast to some other suspensions known in prior art, the formulations of the invention require no surfactant, or only small amounts of surfactant, for their physical stabilisation. This is a significant advantage as surfactants have a substantial potential for irritation and local toxicity, especially when administered by subcutaneous or intramuscular injection or by instillation into the eye. According to one of the preferred embodiments, the compositions of the invention are substantially free of surfactant. In a further embodiment, the total amount of surfactant or surfactants, if more than one surfactant is incorporated, is not more than about 10 wt.-%, in particular not more than about 5 wt.-%, or preferably not more than about 2 wt.-%, respectively. In further preferred embodiments, the amount is not more than about 1 wt.-%, or not more than about 0.5 wt.-%, respectively. In this context, the SFA's as described herein, although they possess some amphiphilic properties due to their chemical structure which includes fluorinated and non-fluorinated alkyl (or alkylene) groups characterised by different degrees of lipophilicity, are not understood as being within the scope of surfactants.

The surfactants which are absent or only present in small amounts include non-ionic, cationic, anionic, and zwitterionic surfactants as commonly used as excipients in various types of pharmaceutical compositions, e.g. as wetting agents, emulsifiers, dispersing agents, solubilisers and the like. Examples of surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, lecithins, purified or synthetic phospholipids, and mixtures of two or more thereof.

The compositions of the invention may optionally comprise a non-fluorinated organic liquid, for example in order to modify the properties of the liquid vehicle, such as the viscosity. Such other liquid may be an oil selected from glyceride oils, liquid waxes, and liquid paraffin, or an organic solvent exhibiting a high degree of biocompatibility, or a mixture of more than one liquid excipients.

Examples of potentially useful oily excipients which may be used in combination with one or more SFA's include triglyceride oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye.

Examples of potentially useful organic solvents include glycerol, propylene glycol, polyethylene glycol, and ethanol. The concentration of the cosolvent should preferably be low relative to that of the SFA or SFA mixture. If an organic solvent such as ethanol is used, it is recommendable to keep it below a level of approx. 5 wt.-%. More preferably, the content of ethanol is from about 0.1 to about 2 wt.-%, and most preferably not more than about 1 wt.-%.

The composition may of course comprise further pharmaceutical excipients as required or useful. Potentially useful excipients include acids, bases, antioxidants, stabilisers, synergists, colouring agents, thickening agents, and—if required in a particular case—a preservative. Generally, however, the invention provides a means of formulating non-aqueous compositions which are microbiologically stable. This is due to the fact that SFA's are not normally prone to microbial contamination. Hence, it is possible to formulate preservative-free compositions to be filled in multi-use containers. Preservative-free compositions are better tolerated by many patients and enable lower costs of final goods.

The liquid suspensions of the invention may be prepared by conventional methods. In principle, the solid particles comprising the active ingredient may be dispersed in the liquid vehicle comprising the SFA. Alternatively, the particles may be precipitated in situ by adding a—typically organic—solution of the active ingredient (and, optionally, one or more solid excipients) under controlled conditions to the SFA-based vehicle.

The particle size of the dispersed phase may be adjusted before or after the particles are combined with the liquid vehicle. In one of the preferred embodiments, particles of the active ingredient are provided which already have the appropriately selected particle size. Powders having such selected particle size may be obtained directly from the synthesis of the respective compound by crystal engineering, or after synthesis by conventional grinding or milling methods using standard equipment such as a ball mill, hammer mill, roller mill, colloidal mill, jet mill, or the like. If the particle size is to be reduced after preparation of a suspension, ultrasonication as well as various types of homogenisers may be used, such as colloid mills or high pressure homogenisers.

The superior physical properties of the suspensions according to the invention render these compositions particularly useful for topical administration to the eye of a patient, to the ear, nose or lung, or parenterally by injection. Preferred modes of injection include dermal, subcutaneous, intramuscular, and locoregional injection. Most preferred are the subcutaneous and intramuscular routes of administration.

Further embodiments will become obvious from the following examples which illustrate the invention in some of its major aspects.

EXAMPLES

Example 1: Stabilisation of α-Chymotrypsinogen A

30 Vials with aliquots of lyophilised α-chymotrypsinogen A (CHY) were prepared from a stock solution of the protein. To each of 10 aliquots, 2.5 mL of potassium phosphate buffer (PPB, 50 mM, pH 8.0) were added, to each of another 10 aliquots, 2.5 mL of F6H8 were added. The remaining 10 vials served as controls. The vials were purged with nitrogen, gently shaken and stored at 50° C. At predetermined intervals, vials were drawn, their content extracted and analysed by circular dichroism and an enzymatic assay.

In result, it was found that the enzymatic activity of the samples stored in buffer was dramatically reduced already after a storage time of 1 day. Agglomeration was visible. In contrast, the SFA sample retained substantial enzymatic activity over a period of weeks. In fact, the bioactivity of CHY stored in F6H8 was very similar to that of the control vials. Table 1 shows the enzymatic activity in units/mL found for each tested sample.

With respect to the circular dichroism results, the samples of CHY stored in F6H8 were highly similar to the controls at all times, whereas the samples of CHY stored in PPS showed significant changes indicating substantial denaturation.

TABLE 1

| Days of storage | CHY in PPB | CHY in F6H8 | CHY controls |
|---|---|---|---|
| 1 | 0.9 | 19.0 | 21.4 |
| 7 | 1.3 | 21.9 | 22.2 |
| 14 | 0.0 | 11.0 | 12.0 |
| 28 | 0.4 | 14.8 | 16.9 |
| 42 | 0.2 | 9.1 | 7.9 |
| 56 | 0.6 | 13.0 | 12.4 |
| 80 | 0.3 | 8.4 | 10.5 |

To aliquots of 2.5 mg of bovine insulin, either 2.5 mL of F6H8 or 2.5 mL of highly diluted aqueous hydrochloric acid (0.04 M) were added and gently shaken. The samples were purged with either nitrogen or oxygen and then stored at 37° C. or 50° C., respectively. At predetermined intervals, vials were drawn, their content extracted and analysed by circular dichroism and an HPLC assay.

Example 2: Stabilisation of Bovine Insulin

In result, it was found that insulin was highly unstable when stored in aqueous hydrochloric acid, but substantially stable at both temperature levels when stored in F6H8, regardless of whether the samples had been purged with nitrogen or oxygen. This was confirmed by both analytical methods. The results of the HPLC assay (in % of recovered insulin) are given in table 2 (storage at 37° C.) and table 3 (storage at 50° C.).

TABLE 2

| Days of storage | Gas | Insulin in HCl | Insulin in F6H8 |
|---|---|---|---|
| 0 |  | 94.0 | 84.8 |
| 1 | Nitrogen | 86.2 | 89.3 |
| 1 | Oxygen | 95.1 | 92.5 |
| 22 | Nitrogen | 1.5 | 84.9 |
| 22 | Oxygen | 1.5 | 91.5 |

TABLE 3

| Days of storage | Gas | Insulin in HCl | Insulin in F6H8 |
|---|---|---|---|
| 0 |  | 94.0 | 84.8 |
| 1 | Nitrogen | 1.1 | 87.9 |
| 1 | Oxygen | 2.2 | 88.8 |

TABLE 3-continued

| Days of storage | Gas | Insulin in HCl | Insulin in F6H8 |
| --- | --- | --- | --- |
| 16 | Nitrogen | 2.2 | 88.4 |
| 16 | Oxygen | 5.5 | 86.7 |
| 22 | Nitrogen | 2.5 | 95.4 |
| 22 | Oxygen | 2.7 | 92.3 |

Example 3: Physical Stability and Redispersibility of Human Insulin Suspensions

In this series of experiments, the physical stability and redispersibility of human insulin (HI) suspensions in an SFA and other non-aqueous liquids were evaluated. As mentioned, the degree of physical stability and in particular the redispersibility are important criteria which determine the suitability of a suspension medium e.g. for an injectable or topically pharmaceutical composition.

The retention of turbidity, of suspensions of human insulin (HI) in F6H8, perfluorodecalin (PFD), perfluorooctane (PFO), and octane (OCT) was determined photometrically by measuring transmittance at 350 nm at various time intervals over a total period of 24 hours (FIG. 1).

Human insulin (Sigma, 12643) was suspended in each of the liquids at a concentration of 0.91 mg/mL. The suspensions were vortexed for 3 seconds, then bath-sonicated in ice for 5 minutes. Immediately after sonication, the suspensions were transferred via pipette into stoppered 3-mL quartz cells. Transmittance at 350 nm was measured using a UV spectrophotometer for each of the suspensions at time intervals over a period of 16 hours. The suspensions were then re-dispersed for 15 minutes using a test tube rotator (Labinco) set at 10 rpm and 45 degree angle. Following re-dispersion, transmittance was measured over a further 8-hour period. The transmittance data measured at 350 nm was normalised against a solution of 0.91 mg/mL human insulin in 0.04M HCl, pH 1.6.

In result, it was observed that phase separation occurred significantly slower for human insulin suspended in F6H8 (FIG. 1). Greater stability of the suspension of human insulin in F6H8, compared to the samples in the perfluorinated solvents and octane was evident in the higher levels of turbidity (as correlated with lower % transmittance values) retained over a longer period of time. In contrast, the suspensions in the perfluorinated solvents and hydrocarbon solvent octane rapidly lost turbidity and showed phase separation (e.g. by flotation or sedimentation) as demonstrated by the sharp rapid increases in transmittance. Heterogeneity could be visibly observed in the sample cells of these solvents, even in the initially formed suspension, with further sedimentation and/or flotation to the liquid-air interface rapidly becoming apparent over time.

After 16 h of standing time, the re-dispersed suspension of human insulin in F6H8 also regained the approximately same level of turbidity as when the suspension was initially formed. In contrast, the same level of turbidity of the perfluorodecalin, perfluorooctane and octane suspensions could not recovered after re-dispersion. Thus, only the suspension of the protein in SFA, but not the suspensions in PFD, PFO and OCT, demonstrated adequate physical properties for pharmaceutical use.

Example 4: Physical Stability and Redispersibility of α-Chymotrypsin Suspensions The retention of turbidity, of suspensions of α-chymotrypsin (CHY) in F6H8, perfluorodecalin (PFD), perfluorooctane (PFO), and octane (OCT) was determined photometrically by measuring transmittance at 350 nm at various time intervals over a total period of 24 hours.

α-Chymotrypsin (Sigma, C4129) was suspended in each of the solvents at a concentration of 2 mg/mL. The suspensions were vortexed for 3 seconds, then bath-sonicated in ice for 5 minutes. Immediately after sonication, the suspensions were transferred via pipette into stoppered 3-mL quartz cells. Transmittance at 350 nm was measured using a UV spectrophotometer for each of the suspensions at time intervals over a period of 16 hours. The suspensions were then re-dispersed for 15-20 minutes using a test tube rotator (Labinco) set at 10 rpm and 45 degree angle. Following re-dispersion, transmittance was measured over a further 8-hour time period. The transmittance data at 350 nm was normalized against a solution of α-chymotrypsin (2 mg/mL) in potassium phosphate buffer, 50 mM, pH 8.

Figure 2:
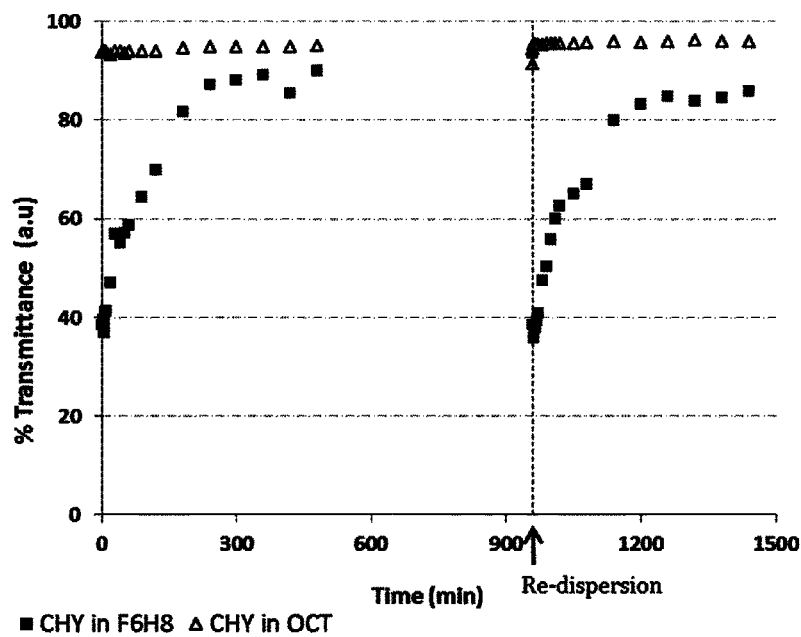
FIG. 2: Retention of turbidity of suspension of α-chymotrypsin (CHY) in F6H8 and octane (OCT).
Figure 3:
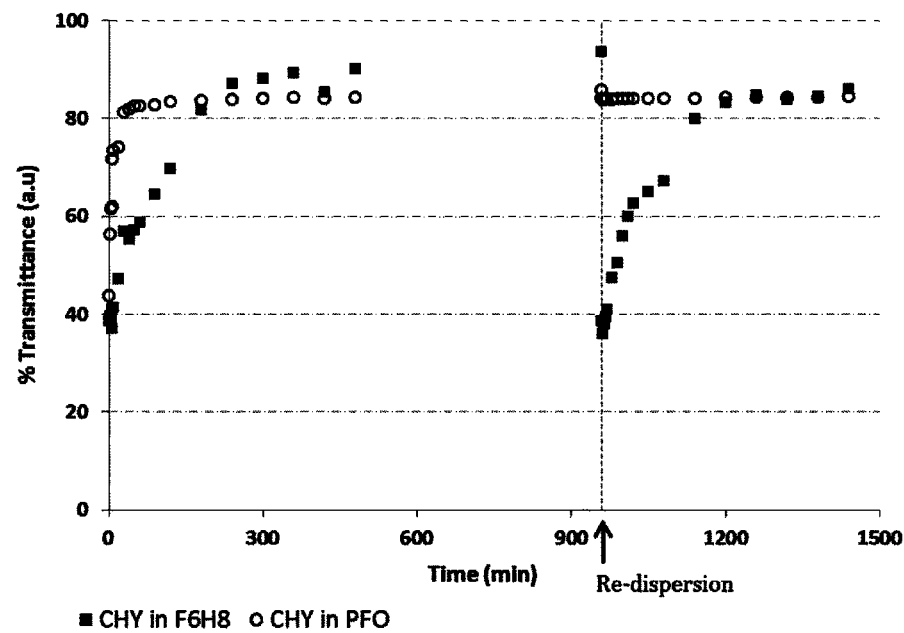
FIG. 3: Retention of turbidity of suspension of α-chymotrypsin (CHY) in F6H8 and perfluorooctane (PFO).
Figure 4:
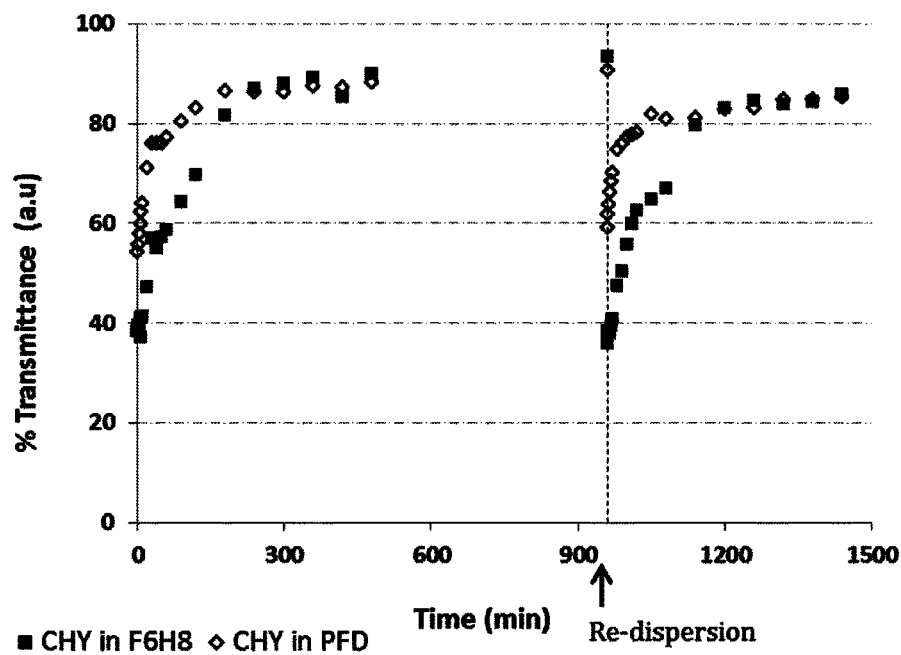
FIG. 4: Retention of turbidity of suspension of α-chymotrypsin (CHY) in F6H8 and perfluorodecalin (PFD).

From the outset, substantially lower values of transmittance were observed for the α-chymotrypsin suspension in F6H8 compared to the respective suspensions in perfluorodecalin (FIG. 3), perfluorooctane (FIG. 4), and octane (FIG. 2), indicating a prolonged homogeneity of this suspension and a slower phase separation (e.g. by flotation or sedimentation) in the case of the SFA suspension. In particular, α-chymotrypsin suspended in octane was observed to rapidly sediment to the bottom of the quartz cell, indicating, indicating very poor to absent suspension characteristics (near 100% transmittance). Also following re-dispersion after standing for a period of 16 hours, the suspension of α-chymotrypsin in F6H8 was clearly superior to the other suspensions in that its original suspension turbidity (at t=0) was largely recovered, in contrast to that of the other suspensions.

Example 5: Suspension Kinetics of Bovine Serum Albumin Suspensions

In a similar manner as in Examples 3 and 4, the suspension kinetics of bovine serum albumin (BSA) in F6H8, perfluorodecalin (PFD), perfluorooctane (PFO), and octane (OCT) was evaluated by measuring the transmittance at 350 nm at various time intervals over a period of 2 hours.

BSA was suspended in each of the solvents at a concentration of 5 mg/mL. The suspensions were vortexed for 3 seconds, then bath-sonicated in ice for 5 minutes. Immediately after sonication, the suspensions were transferred via pipette into stoppered 3-mL quartz cells. Transmittance at 350 nm was measured using a UV spectrophotometer for each of the suspensions at time intervals over a period of 2 hours. The transmittance data at 350 nm was normalized against a solution of BSA (5 mg/mL) in sodium phosphate buffer, pH 7.

Figure 5:
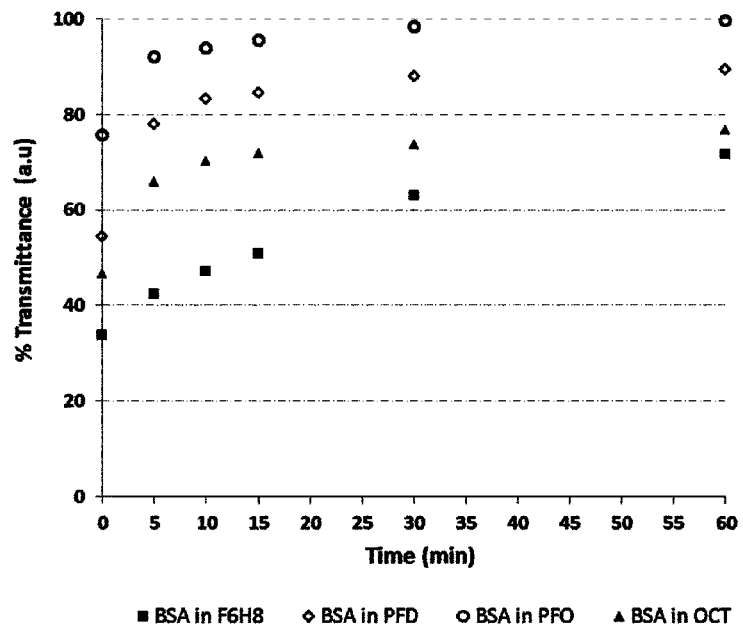
FIG. 5: Retention of turbidity of suspensions of bovine serum albumin (BSA) in F6H8, perfluorodecalin (PFD), perfluorooctane (PFO), and octane (OCT).

In result, the suspension of BSA in F6H8 was observed to have the lowest initial level of transmittance (FIG. 5). Moreover, the increase in transmittance within the first testing intervals (5 and 10 minutes) was relatively low for the SFA-based suspension compared to that of the other suspensions which were already closer to their plateau levels at these time points. In pharmaceutical terms, these differences translate into a prolonged time that is available for conveniently administering a dose of such suspension of BSA in the SFA e.g. by subcutaneous injection, which is typically accomplished within a few minutes.

Example 6: Suspension Kinetics of Salmon Calcitonin Suspensions

The retention of turbidity of suspensions of salmon calcitonin (sCT) in F6H8, perfluorodecalin (PFD), perfluorooctane (PFO), and octane (OCT) was determined photometrically by measuring transmittance at 350 nm at various time intervals over a period of 2 hours.

Salmon calcitonin was suspended in each of the solvents at a concentration of 5 mg/mL. The suspensions were vortexed for 3 seconds, then bath-sonicated in ice for 5 minutes. Immediately after sonication, the suspensions were transferred via pipette into stoppered 3-mL quartz cells. Transmittance at 350 nm was measured using a UV spectrophotometer for each of the suspensions at time intervals over a period of 2 hours. The transmittance data at 350 nm was normalized against a solution of salmon calcitonin (5 mg/mL) in phosphate buffered saline, pH 7.4.

Figure 6:
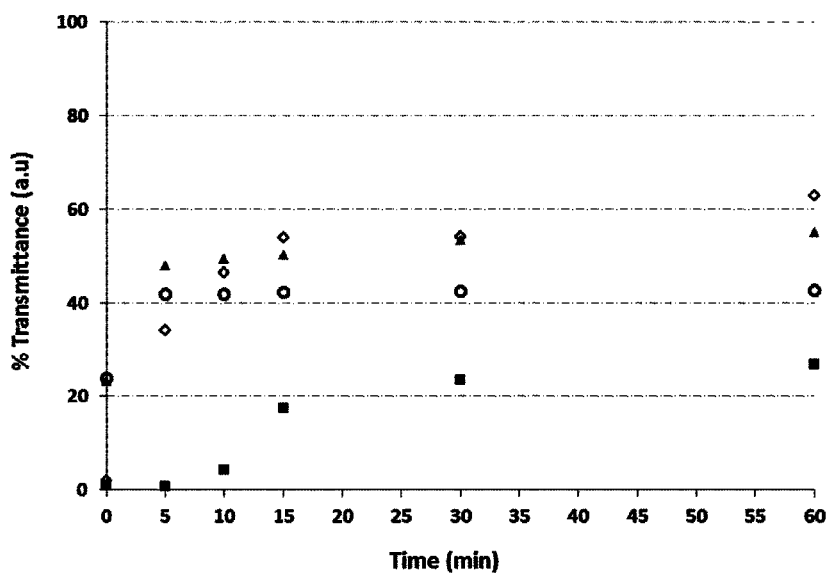
FIG. 6: Retention of turbidity of suspensions of salmon calcitonin (sCT) in F6H8, perfluorodecalin (PFD), perfluorooctane (PFO), and octane (OCT).

The suspension of sCT in F6H8 was observed to have the lowest initial level of transmittance, as well as over a period of 2 h, again indicating substantially superior suspension properties compared to the suspensions in PFD, PFO and OCT (FIG. 6).

Example 7: Size Distribution of Human Insulin in F6H8

Dynamic light scattering (DLS) measurements of samples of human insulin (Sigma Aldrich 10908) in F6H8 were taken using a Nanostar™ Wyatt Technology DLS instrument. The measurements were taken using 4 μL disposable cuvettes. Samples were prepared at concentrations of 1 mg/mL and 10 mg/mL, and were not filtered prior to the taking of measurements.

Figure 7:
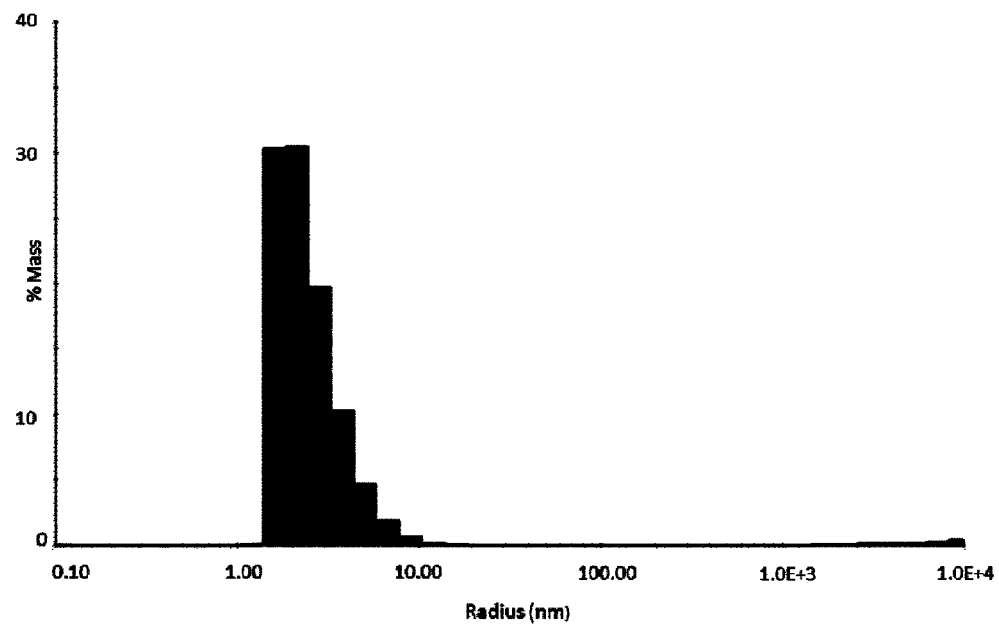
FIG. 7: Dynamic light scattering (DLS) measurements of human insulin in F6H8 at 1 mg/mL.
Figure 8:
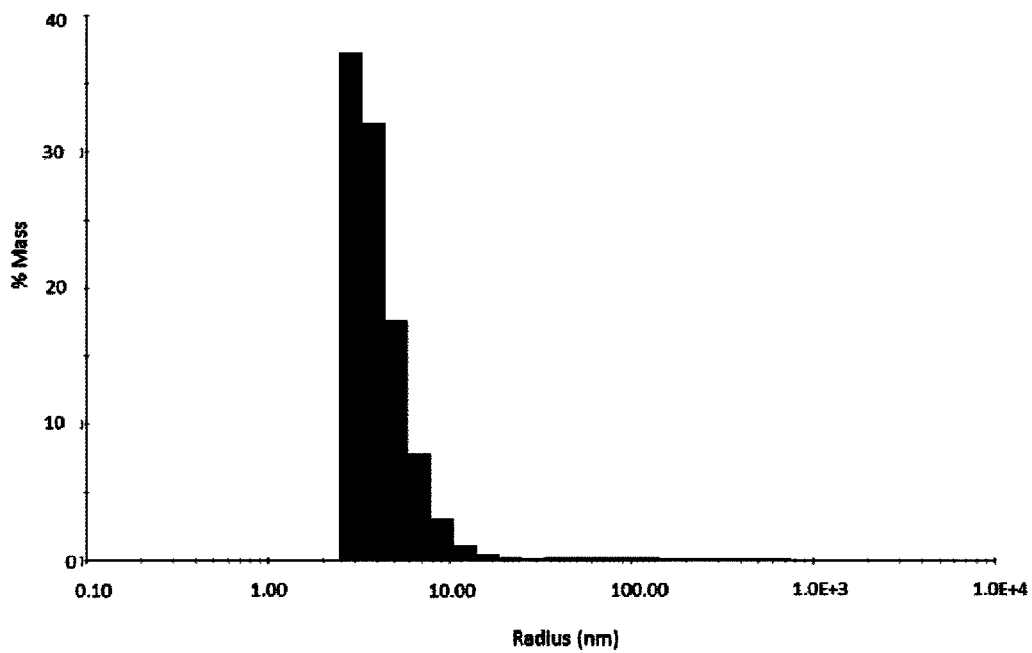
FIG. 8: Dynamic light scattering (DLS) measurements of human insulin in F6H8 at 10 mg/mL.

Results from the samples at both concentrations demonstrate that there is some solvation of human insulin in F6H8, with a significant fraction with particle size correlating with the monomeric forms of the protein (FIG. 7—size distribution of human insulin in the 1 mg/mL sample (Run #1) and FIG. 8—size distribution of human insulin in the 10 mg/mL sample). It is believed by the inventors that the ability of the SFA to solvate the protein contributes to the advantageous dispersion or suspension properties and prevents the formation of coarse aggregates which are not re-dispersible.

TABLE 4

| Sample | Average Radius (nm) | % Mass Monomer Peak |
| --- | --- | --- |
| 1 mg/mL, Run # 1 | 2.6 | 98.4 |
| 1 mg/mL, Run # 2 | 3.5 | 100 |
| 10 mg/mL | 4.3 | 99.4 |

Example 8: Size Distribution of Human Calcitonin in F6H8

Dynamic light scattering (DLS) measurements of samples of human calcitonin (Bachem AG 4014409.00005) in F6H8 were taken using a Nanostar™ Wyatt Technology DLS instrument. The measurements were taken using 4 μL disposable cuvettes. A sample was prepared at a concentration of 1 mg/mL. The sample was not filtered prior to the taking of measurements.

Figure 9:
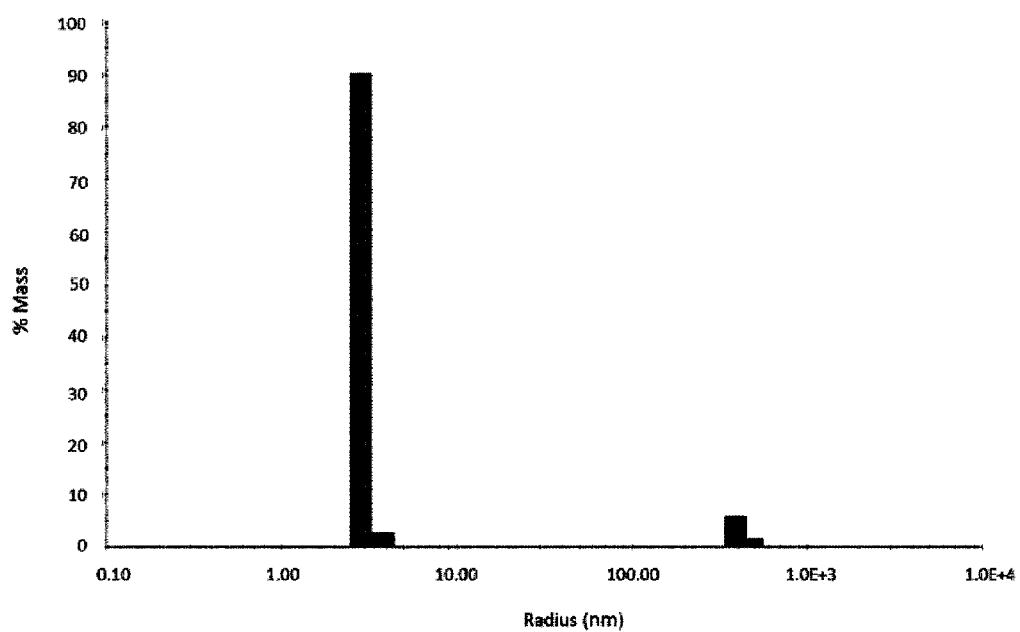
FIG. 9: Dynamic light scattering (DLS) measurements of human calcitonin in F6H8 at 1 mg/mL.

Results from the sample demonstrate that there is some solvation of human calcitonin in F6H8 with a detectable fraction with particle sizes correlating with the monomeric forms of the protein (FIG. 9). Small aggregates were also detected. Again, it is believed that the solvation of the protein by the SFA contributes to the advantageous dispersion or suspension properties and prevents the formation of coarse irreversible aggregates.

The invention claimed is:

1. Composition comprising a bioactive compound and a liquid vehicle, wherein the liquid vehicle comprises a semifluorinated alkane of the formula

RFRH wherein RF is a linear perfluorinated hydrocarbon segment with 4 to 12 carbon atoms, and wherein RH is a linear alkyl group with 4 to 8 carbon atoms; and wherein the bioactive compound is a therapeutic or diagnostic agent or vaccine selected from polypeptides and proteins having a molecular mass of at least 1,500 Da, dispersed or suspended in the liquid vehicle;
   wherein the semifluorinated alkane is selected from the group consisting of F4H5, F4H6, F4H8, F6H4, F6H6, F6H8, and F6H10.

2. The composition of claim 1, wherein the bioactive compound is sensitive to degradation and/or aggregation.

3. The composition of claim 1, wherein the bioactive compound is a single-domain protein or a two-domain protein.

4. The composition of claim 1, wherein the bioactive compound is an insulin.

5. The composition of claim 1, wherein the semifluorinated alkane is selected from F4H5 and F6H8.

6. The composition of claim 1, wherein the composition is substantially free of water.

7. Method of preparing a composition comprising a bioactive therapeutic or diagnostic agent or vaccine selected from a polypeptide or protein, comprising the step of incorporating the bioactive polypeptide or protein within a liquid vehicle which comprises a semifluorinated alkane of the formula

RFRH wherein RF is a linear perfluorinated hydrocarbon segment with 4 to 12 carbon atoms, and wherein RH is a linear alkyl group with 4 to 8 carbon atoms such as to form a dispersion or suspension;
   wherein the bioactive compound is a therapeutic or diagnostic agent or vaccine selected from polypeptides and proteins having a molecular mass of at least 1,500 Da, dispersed or suspended in the liquid vehicle; and
   wherein the semifluorinated alkane is selected from F4H5, F4H6, F4H8, F6H4, F6H6, F6H8, and F6H10.

8. The method of claim 7, wherein the bioactive polypeptide or protein is sensitive to degradation and/or aggregation.

9. The method of claim 7, wherein the composition is chemically and/or physically stabilised.

10. The composition of claim 4, wherein the semifluorinated alkane is selected from F4H5 and F6H8.

11. The composition of claim 10, wherein the composition is substantially free of water.

12. The composition of claim 1, wherein the polypeptide or protein has a molecular mass of at least about 2,000 Da.

13. The method of claim 7, wherein the polypeptide or protein has a molecular mass of at least about 2,000 Da.

14. The composition of claim 1, wherein the semifluorinated alkane is F6H8.

15. The composition of claim 4, wherein the semifluorinated alkane is F6H8.

16. The composition of claim 1, wherein the bioactive compound is sensitive to degradation and/or aggregation, and wherein the bioactive compound is easily re-dispersed by gentle shaking after flotation or sedimentation.

* * * * *